(12) United States Patent
Schachter et al.

(10) Patent No.: US 7,785,249 B2
(45) Date of Patent: Aug. 31, 2010

(54) BIOFEEDBACK METHOD AND APPARATUS

(75) Inventors: Robert S. Schachter, Brooklyn, NY (US); John Rose, New York, NY (US)

(73) Assignee: Theta Technologies, LLC, New York, NY (US)

( * ) Notice: Subject to any disclaimer, the term of this patent is extended or adjusted under 35 U.S.C. 154(b) by 394 days.

(21) Appl. No.: 11/860,798

(22) Filed: Sep. 25, 2007

(65) Prior Publication Data

US 2008/0071137 A1    Mar. 20, 2008

Related U.S. Application Data

(63) Continuation of application No. PCT/US2006/011279, filed on Mar. 27, 2006.

(60) Provisional application No. 60/665,393, filed on Mar. 28, 2005.

(51) Int. Cl.
*A61M 21/00* (2006.01)
(52) U.S. Cl. .......................... 600/27; 600/534; 128/905
(58) Field of Classification Search ............. 600/26–28, 600/529, 534–545, 300; 607/207.23–207.25; 128/905
See application file for complete search history.

(56) References Cited

U.S. PATENT DOCUMENTS

| | | | |
|---|---|---|---|
| 4,665,926 A | 5/1987 | Leuner | 128/716 |
| 5,076,281 A | 12/1991 | Gavish | 128/721 |
| 5,219,322 A | 6/1993 | Weathers | 600/27 |
| 5,304,112 A | 4/1994 | Mrklas | 600/27 |
| 5,343,871 A | 9/1994 | Bittman et al. | 128/732 |
| 5,518,497 A | 5/1996 | Widjaja et al. | 600/27 |
| 6,090,037 A | 7/2000 | Gavish | 600/27 |
| 2001/0000459 A1 | 4/2001 | Kania | 381/98 |

FOREIGN PATENT DOCUMENTS

GB    1359005    7/1974

*Primary Examiner*—John P Lacyk
(74) *Attorney, Agent, or Firm*—Fitzpatrick, Cella, Harper & Scinto

(57) ABSTRACT

The invention is directed to a method and apparatus for relieving stress using biofeedback techniques. In embodiments, the method and system are used according to a specified regimen to enable a user to achieve a relaxed state. The apparatus comprises a sensor 10 wirelessly connected to a CPU 20, which processes signals from the sensor 10 to produce a visual display 36 and/or auditory display 44 that is representative of the relaxation state of the user.

21 Claims, 1 Drawing Sheet

BIOFEEDBACK METHOD AND APPARATUS

This application is a continuation of International Application No. PCT/US2006/011279, filed Mar. 27, 2006, which claims the benefit of priority of provisional application No. 60/665,393, filed Mar. 28, 2005, both of which applications are incorporated by reference in their entirety.

BACKGROUND OF THE INVENTION

1. Field of the Invention

The invention is directed to a method wherein a repeated biofeedback regimen is used to achieve a deeply relaxed state. Moreover, after repeated use of the method described herein, the user is able to achieve this deeply relaxed state without using the device described herein. In another aspect, the repeated regimen is used in conjunction with visualization techniques to enhance the individual's performance at sports or other activity. In still another aspect, the invention is directed to an apparatus adapted for use with these methods.

2. Description of the Related Art

A relaxation therapy apparatus is described in GB 1,359,005, which is incorporated herein by reference. The apparatus is said to be useful in "treating psychical and psychosomatic illness, general nervousness, and states of exhaustion."

U.S. Pat. No. 4,665,926, also incorporated herein by reference, describes a method and apparatus for measuring the relaxation state of a person.

According to the foregoing patents, a respiration sensor is used to obtain a signal from a subject's breathing characteristics and a calculation is performed to obtain a measure characteristic of the subject's relaxation state, referred to herein as the relaxation quotient or "RQ." The signal is processed to form a sensory output, qualitatively corresponding to the subject's relaxation state. The sensory output is passed to a sensory stimulus generator, such as a lamp, which is observed or experienced by the subject, creating a biofeedback loop.

The prior art methods have not been used outside the clinical setting, or with systematic repetition for the purpose of managing stress, or in conjunction with visualization techniques to enhance performance at sports or other activities. The present method is based on the repeated application of these relaxation techniques to produce a body memory or mental image imprint, which aids the user in effective stress management, or to enhance performance in sports, business, or other activity.

The prior art devices utilize hard-wired, analog equipment, not adapted for streamlined use outside the clinical setting. Accordingly, the novel adaptation of the apparatus for the aforesaid purposes forms another aspect of the invention.

SUMMARY OF THE INVENTION

In one aspect, the invention is a method of inducing a relaxed state, which comprises the steps of: detecting a user's breathing pattern with a sensor worn by or positioned on the user; producing a signal corresponding to the breathing pattern detected by the sensor; generating auditory and/or visual outputs corresponding to the signal, and transmitting the auditory and/or visual outputs to the user through a a feedback monitor worn by, or otherwise proximate to, the user. These steps are then repeated at specified intervals for specified lengths of time to create a body memory or mental image in the user.

In a normal waking and stimulated state, brainwaves (as measured with an EEG), are in a range of about 15 cycles per second to about 40 cycles per second. Relaxation occurs in the alpha state, where brainwaves are in a range of about 9 cycles per second to about 14 cycles per second. A "deeply relaxed state" is used herein to describe the theta state, where brainwaves are in a range of about 5 to about 8 cycles per second. The theta state is typical of a trance state, similar to what occurs in a hypnotized subject. Depending on the individual, achieving either a theta or alpha state will enhance athletic performance. It also has the additional benefit of lowering the individual's state of stress. The relaxed or deeply relaxed state is achieved by utilizing the device described herein, in the manner described herein. Unless specified otherwise, "relaxed state" is used herein to refer to both alpha and theta states.

As described in the aforesaid U.S. Pat. No. 4,665,926, the relaxation quotient is the quotient or ratio of the time period corresponding to the inhalation/exhalation phase of the user's respiratory cycle $t_A$ divided by the time period corresponding to the pause or interval in the cycle $t_P$ averaged over a fixed period of 0.5 minutes to 3 minutes. Applicants have found that the relaxation quotient obtained according to the presently described methods and apparatus correlates with brainwave patterns, such that an RQ of greater than about 29 corresponds to the theta or deeply relaxed state; an RQ in a range of about 15 to about 29 is indicative of the relaxed alpha state; and an RQ in a range of about zero to about 14 indicates a normal, waking, non-relaxed beta state brainwave.

The invention comprises a visualization component, a relaxation component and a repetition component. With regard to the visualization component, this involves running an application-specific visualization observed by the user. The relaxation component comprises the steps of detecting a user's breathing pattern with a sensor worn by the user; producing a signal corresponding to the breathing pattern detected by the sensor; processing the signal to generate auditory and/or visual outputs corresponding to the relaxation state of the user; and transmitting the auditory and/or visual outputs to the user through a feedback monitor worn by the user.

With regard to the repetition component, applicants have found that using this device repetitively within a concentrated period of time produces a systemic change that results in the user's ability to relax at will, without employing the device, and thereby either enhance performance or manage stress. This occurs as a result of recalling a body memory or mental image resulting from the experience that allows the user to induce these states of relaxation without the use of the device. This repetition may cause an individual to relive the positive mental impressions associated with a well-performed task, such as hitting a home run at baseball or getting a goal from the blue line at ice hockey. This response will enable the user to control his or her level of emotional arousal in any situation in which he or she might feel anxiety that would contribute to poor performance in a specific task. Thus, the response enables an individual to better manage stress and, in combination with sports visualization techniques, to improve performance at sports.

The inventive apparatus for practicing these methods comprises: a respiration sensor worn by a user that produces signals corresponding to the depth and frequency of the user's breathing; a processor adapted to digitally process the signals produced by the respiration sensor into audio and/or visual outputs, and to convert the signals from the respiration sensor into a quantitative measure of the user's relaxation state; (optionally) a memory store that will enable the user to review the relaxation pattern/results over the course of the entire session (and prior sessions); a feedback monitor worn by (or proximate to) the user and adapted to display visual and/or auditory images corresponding to an output signal formed by the processor. The feedback monitor and the sensor are adapted to communicate wirelessly with the processor.

The apparatus described herein includes digital components and processing, and utilizes wireless technology to connect the components. In addition, it incorporates an audio-visual playback and display capability to be used in the pre-relaxation visualization. In further embodiments, the apparatus includes components for capturing, storing and displaying data. These novel features, as described in the following detailed description, are well adapted for the use of the system in repeated sessions to create a conditioned response, for the purposes described herein.

DETAILED DESCRIPTION OF THE INVENTION

Figure 1:
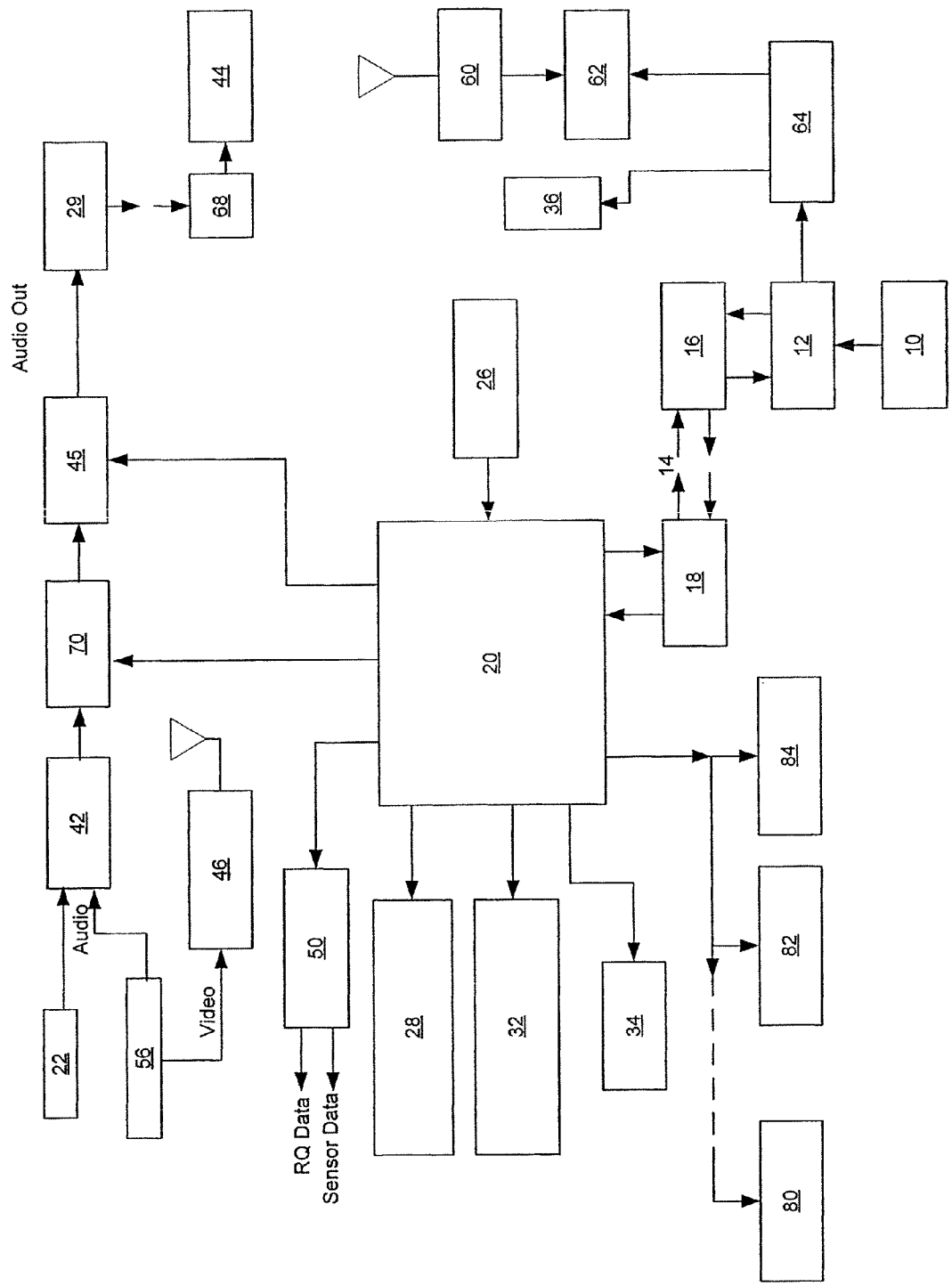
FIG. 1 is a schematic diagram of an apparatus according to the invention.

The apparatus comprises a sensor that measures small movements of the diaphragm as the user breathes, an electronic control, a transducing means, and a sensory stimulus generator that produces a light and sound through a feedback monitor. A feedback monitor is a device capable of displaying the produced light and/or sound output to the user. Examples of a feedback monitor include, without limitation, a separate eyepiece, a separate earpiece, or a headset which incorporates either or both. It is preferable that the feedback monitor be worn by the user, or that it be proximate to the user to a degree sufficient to allow user perception of the feedback monitor. The result is that the apparatus provides a feedback loop such that the amplitude of the light and sound production is connected to and is directly proportional to the amplitude of the breathing.

As shown in FIG. 1, respiration sensor 10, worn by a user, detects the user's breathing patterns. Instead of the "measuring band" disclosed in the prior art for this purpose, which encircles the user's chest, it is preferred to use an optical encoder, of a type available from U.S. Digital Corporation, Vancouver, Wash., for example. However, the type of transducer technology used is not critical and several such technologies are known in the art and may be adapted for this purpose, including without limitation, accelerometers, infrared or ultrasonic devices, and strain gauges.

The signal produced by the respiration sensor is transmitted wirelessly to the CPU 20 in digital format. The signal preferably is processed for wireless transmission by a microprocessor 12, of a type available from BasicX (NetMedia Inc., Tucson, Ariz.) or other vendors. Two-way wireless transmission, shown as dashed lines 14, is preferred, for example via Bluetooth® transceiver protocol 16, 18, or other available wireless format or protocols. The CPU 20 is a conventional microprocessor capable of digitally processing the signal transmitted from the sensor to form output signals to drive components of the audio display 44 and visual display (lights) 36. It is also preferred to transmit audio to the audio display 44 via wireless connection 29, 68. These displays may be conveniently worn by the user. Such devices are known in the art and are commercially available.

In preferred embodiments, the apparatus has rich audio and video display capabilities which make the apparatus more user-friendly and better adapted for use with visualization techniques. For example, a CD or DVD player 56 is adapted to provide background music while the user is wearing the feedback monitor, via audio source select 42. In embodiments, the CD or DVD player is a DVD player adapted to provide application-specific visualizations. These visualizations (described at greater length below) may be transmitted via video transmitter 46 to a video receiver 60 (or by other means, including wired transmission) to a video screen 62. Alternatively, and most preferably, such visualizations from the DVD player 56 are displayed in the feedback monitor itself. These external sources of audio and video may be provided with separate controls 45, 64. "External source" of audio and video, in this context, simply means that the audio and video from the CD or DVD player is not modified based on the signals from the respiration sensor.

There are two types of additional audio and one type of additional visual stimulation used with the device, beyond the audio/video used for the visualization. On the one hand, there is a CD or DVD source of audio that produces background sounds which do not vary with respiration. Use of this invariant background sound is preferred, in order to further isolate the user and enhance the impact of the modulated white noise and visual stimulation, as described herein. On the other hand a nonspecific "white noise" waveform generated at 22 varies according to amplitude of the respiration. This waveform is modulated in a sensor signal modulator 70 according to a signal corresponding to relaxation quotient obtained from the user coming from CPU 20. That is, the white noise audio volume varies according to the rise and fall of the user's breathing depending on the modulation selected. In addition, the visual stimulus is also modulated in parallel with the audio. There is no particular pattern or format of the light and sound waveform that is used, as it directly mirrors the rhythm of breathing.

In the embodiment of FIG. 1, two-way communication of the CPU with the light/video selector/driver 64 permits a creation of a visual display 36 in the feedback monitor that corresponds with an output signal from the CPU derived from a measure of user's breathing. Light display 36 varies in intensity (amplitude) and/or color depending on the rise and fall in intensity of the user's respiration. The RQ from the sensor is preferably determined in accordance with the algorithm described in the aforesaid U.S. Pat. No. 4,665,926, which is not elaborated upon herein.

Other technological features have been found to be useful in novel combinations in the apparatus. Printer 34 may be used to record sensor data or RQ data from the CPU 20. Memory modules 80, 82, 84 may be used to record sessions, which is particularly useful in the context wherein the user follows a regimen of sessions with the apparatus. Front panel switches 26, LED display 32 and/or LCD display 28 are additional user-friendly components of the apparatus, useful as the apparatus finds application outside the clinic. A dual serial digital analog converter 50 adds the capability of outputting sensor or RQ data. The apparatus of the invention is not limited to the schematic depicted in FIG. 1 and need not contain all of the features shown in FIG. 1 to be used effectively for the purposes described herein.

Turning to the methods, applicants have found that using this device repetitively within a concentrated period of time (e.g., using it for 30 minutes 3-4 times per week for 3-4 weeks) produces a systemic change that results in the user's ability to achieve a deeply relaxed state and thereby enhance their ability to manage stress or enhance sports related performance. Repeated sessions with the device are important to the imprinting of the desired response. In preferred embodiments a session lasts about 15 minutes to about 1 hour, in which a feedback monitor is positioned on the user, who is instructed to breathe normally. The device provides a feedback loop such that the amplitude of the light and sound production is correlated to the amplitude and frequency of the user's breathing pattern. As the session progresses the user enters a state of deep relaxation similar to that attained under hypnosis or by autogenic training.

The session is repeated at least twice. The session may be repeated on a daily basis, and may form part of an ongoing regimen of stress reduction or performance enhancement, which may not have specific endpoint. Preferably, the session is repeated multiple times per week. Alternatively, in embodiments, a regimen of stress reduction comprises repeating the session about 10 to about 20 times over the course of 2 to about 6 weeks. The method has been shown to be effective in the context of improving sports performance with a regimen of sessions lasting about 30 minutes, repeated 3 to 4 times per week for 3 to 4 weeks.

There are a wide range of repetitive patterns that produce different effects or degrees of impact that can be tailored to specific results desired. One example is that after approximately twelve uses, the person is asked to picture the feeling attained while using the device at any time or in any situation in which there is tension or anxiety. Additionally, he or she may be asked to take a deep breath at those times. The breath can serve as an associative cue that triggers a body memory of the relaxed state which impels the user to re-create that state, thereby decreasing stimulation of the sympathetic nervous system. The result is less physiological arousal in response to the situation. Essentially, the user becomes accustomed to assuming the relaxed state in response to stress.

For stress management applications, after training is completed, the user is initially taught to visualize the relaxed state or to use a breath as the cue to create a more relaxed state in any situation where there is tension. The individual tracks physical cues that are associated with tension. Eventually, the person attains the relaxed state without consciously using a cue. In this aspect, the method relies on the formation of a conditioned response in a manner that is familiar to psychologists, quite distinct from the prior use of the relaxation machine.

The applicants have discovered that the specific use of the apparatus and method as described herein enhances athletic or sports performance.

A first step in a method for improvement of sports performance is the presentation to the user of an application-specific visualization. An "application specific visualization" is a video presentation focused on an area in which it is desired to improve an individual skill, or set of skills. For example, if the user wishes to improve his or her performance in basketball, the visualization might include video segments in which a perfectly executed basketball foul shot is shown prior to the session. This may be followed by the same segment in a loop, or (for example only), a video segment depicting a perfectly executed lay-up or three-point shot. Likewise, if tennis is the application in which it is desired to improve performance, the video segments might show a perfectly executed serve, forehand or backhand. In golf, the segments might show a tee-shot, a chip shot or putt. The common factor is that the visualization is a focused presentation in the area in which the user wishes to enhance performance. This visualization may be presented in the feedback monitor worn by the user, or on a separate module in the vicinity of the relaxation machine. The external video source may be any source capable of playing back video DVD or any other medium of visual representation and does not need to form part of the apparatus. However, for ease of use it is preferred that this video source is integrated physically within the device.

After the visualization is completed, the user uses the apparatus as described above. The length and repetitions of the session is the same as in the stress management method described above, with the preferred length of a session lasting from about 15 minutes to about 1 hour, with about 30 minutes being preferred. The sessions are repeated at least twice, and in some instances may be repeated as long as the user desires, on an ongoing basis. It is preferred that the sessions be repeated multiple times weekly. Most preferred, a regimen of about 10 to about 20 sessions over 2 two about 6 weeks is preferred. It is not necessary that the visualization is run prior to every session. In some cases, the user may conduct a few sessions with the apparatus before using it with the visualizations.

In a test study with a women's college basketball team, the team members were randomly assigned to two groups, and one group was trained using the system of the present invention. Training consisted of three sessions per week for four weeks. Prior to each of sessions 5 through 12, a short videotape demonstrating a perfect shot from the foul line was shown. At the end of the season, statistics between both groups were compared. The statistics from the group that used the method of this invention exceeded those of the other group in every category of play.

The relaxation training has application in several areas where reaction to stress is an issue, including but not limited to business, medicine and military arenas.

The methods and apparatus may be used in business to improve focusing skills, negotiation skills, and organization skills, which can result in improved worker productivity. The techniques have application to reducing burnout, decreasing employee absenteeism, decreasing employee turnover, decreasing industrial accidents and alcohol abuse among employees.

For medical applications this device is useful in treating a range of disorders exacerbated or caused by stress in which the application of alpha/theta brainwave training has proven to be effective using traditional EEG approaches. These applications include, without limitation, Crohn's disease, Irritable Bowel Syndrome, insomnia, post-traumatic stress disorder and substance abuse.

The methods and apparatus described herein are also useful in connection with dental procedures. In such instances, the feedback monitor including the visual display mounted to the top of the dental chair extending over the patient's head instead of in an eyepiece or headset. One or more earpieces are worn and the respiration sensor is placed over the diaphragm. The light and sound production occurs in the way previously described, in direct proportion to the depth and duration of breaths, thereby creating a relaxed state that makes the dental experience more pleasant.

For military personnel, there are applications to enhance effectiveness and counter fatigue. Training with the device enables one to cope more effectively with stressful situations. In situations where there is combat related fatigue with excitement that prevents restful sleep, the device can be used daily in accordance with the disclosure set forth herein to create a state of relaxation prior to sleep.

The performance enhancement methods according to the invention find application across the spectrum of recreational, amateur, semi-professional and professional sports.

The foregoing description is not to be considered as limiting the invention, which is defined in the appended claims.

The invention claimed is:

1. A method of inducing a relaxed state, comprising:
(a) detecting a user's breathing pattern with a sensor worn by or positioned on the user;

(b) producing a signal corresponding to the breathing pattern detected by the sensor;
(c) generating auditory and/or visual outputs corresponding to the signal, and
(d) transmitting the auditory and/or visual outputs to the user through a feedback monitor, and
(e) repeating steps (a) through (d) at intervals, wherein
  (i) a white-noise audio output that varies according to the user's breathing pattern, and (ii) background music or tones that do not vary according to the user's breathing pattern are transmitted to the user.

2. The method of claim 1, wherein steps (a) through (d) are repeated in a session lasting about 15 minutes to about 1 hour.

3. The method of claim 2, further comprising repeating the session multiple times per week.

4. The method of claim 2, further comprising repeating the session on a daily basis.

5. The method of claim 2, further comprising repeating the session in a regimen of about 10 to about 20 sessions over the course of about 2 to about 6 weeks.

6. The method of claim 2, wherein the session is about 30 minutes, repeated 3 to 4 times per week for 3 to 4 weeks.

7. The method of claim 1, wherein the step of transmitting auditory and/or visual outputs to the user comprises wirelessly transmitting signals to the feedback monitor worn by the user.

8. The method of claim 1, wherein the step of transmitting auditory and/or visual outputs to the user comprises wirelessly transmitting visual signals to an eyepiece monitor worn by the user.

9. The method of claim 8, further comprising transmitting auditory outputs to a separate earpiece worn by the user.

10. The method of claim 1, wherein the step of detecting a user's breathing pattern comprises wirelessly transmitting a signal from a sensor worn by the user to a central processing unit.

11. The method of claim 1, further comprising recording information related to the user's breathing pattern over time in a digital memory device.

12. A method of enhancing the sports performance of a user in a specific application, comprising:
  (a) running an application-specific visualization observed by the user;
  (b) detecting a user's breathing pattern with a sensor worn by the user;
  (c) producing a signal corresponding to the breathing pattern detected by the sensor;
  (d) processing the signal to generate auditory and/or visual outputs corresponding to the relaxation state of the user; and
  (e) transmitting the auditory and/or visual outputs to the user through a feedback monitor worn by the user, and
  (f) repeating steps (a) through (e) at intervals.

13. The method according to claim 12, wherein the application-specific visualization is transmitted through the feedback monitor worn by the user.

14. The method according to claim 12, wherein the application in which performance is enhanced is a sport, and the application-specific visualization is a video presentation of several seconds to 30 minutes in length depicting a specific skill or a small set of specific skills.

15. The method according to claim 14, wherein steps (d) through (e) are repeated in a session lasting about 15 minutes to about 1 hour.

16. The method of claim 15, further comprising repeating the session multiple times per week.

17. The method of claim 15, further comprising repeating the session on a daily basis.

18. The method of claim 15, further comprising repeating the session in a regimen of about 10 to about 20 sessions over the course of about 2 to about 6 weeks.

19. The method of claim 15, wherein the session is about 30 minutes, repeated 3 to 4 times per week for 3 to 4 weeks.

20. The method of claim 1, wherein a theta state is induced in the user.

21. The method of claim 12, wherein a theta state is induced in the user.

* * * * *